(12) United States Patent
Duran et al.

(10) Patent No.: US 7,238,807 B2
(45) Date of Patent: Jul. 3, 2007

(54) PROCESS FOR THE MANUFACTURE OF FUSED PIPERAZIN-2-ONE DERIVATIVES

(75) Inventors: Adil Duran, Rissegg (DE); Guenter Linz, Mittelbiberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/284,836

(22) Filed: Nov. 22, 2005

(65) Prior Publication Data

US 2006/0122393 A1 Jun. 8, 2006

(30) Foreign Application Priority Data

Dec. 2, 2004 (DE) ................... 10 2004 058 337

(51) Int. Cl.
 *C07D 475/00* (2006.01)
 *C07D 239/30* (2006.01)
(52) U.S. Cl. ...................... 544/257; 544/231
(58) Field of Classification Search ................ 544/257, 544/231
 See application file for complete search history.

(56) References Cited

FOREIGN PATENT DOCUMENTS

WO   WO 96/36597   11/1996
WO   WO 03/020722 A1   3/2003

OTHER PUBLICATIONS

Tenbrink, R. E. et. al., "Antagonist, Partial Agonist, and Full Agonist Imi8dazo[1,5-a]quinoxaline Amides and Carbamates Acting through the GABA a/Benzodiazepine Receptor", J. Med. Chem, 1994, 37, 758-768.

*Primary Examiner*—Mark L. Berch
*Assistant Examiner*—Susanna Moore
(74) *Attorney, Agent, or Firm*—Michael Morris; Mary-Ellen M. Devlin; Anthony P. Bottino

(57) ABSTRACT

Disclosed are processes for the preparation of fused piperazin-2-one derivatives of general formula (I)

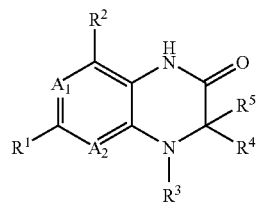

wherein the groups $R^1$ to $R^5$, $A_1$ and $A_2$ have the meanings given in the claims and in the description, particularly the preparation of 7,8-dihydro-5H-pteridin-6-one derivatives and intermediates thereof.

14 Claims, No Drawings

PROCESS FOR THE MANUFACTURE OF FUSED PIPERAZIN-2-ONE DERIVATIVES

APPLICATION DATA

This application claims priority to German application DE 10 2004 058 337.4 filed Dec. 2, 2004.

The invention relates to a process for preparing fused piperazin-2-one derivatives of general formula (I)

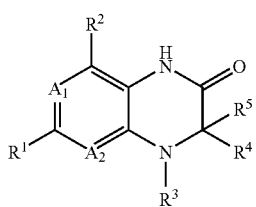

(I)

wherein the groups $R^1$ to $R^5$ have the meanings given in the claims and specification, particularly a process for preparing 7,8-dihydro-5H-pteridin-6-one derivatives.

BACKGROUND TO THE INVENTION

Pteridinone derivatives are known from the prior art as active substances with an antiproliferative activity. WO 03/020722 describes the use of dihydropteridinone derivatives for the treatment of tumoral diseases and processes for preparing them.

7,8-Dihydro-5H-pteridin-6-one derivatives of formula (I) are important intermediate products in the synthesis of these active substances. Up till now they have been prepared using methods involving reduction of nitro compounds of formula (II) below, which led to strongly coloured product mixtures and required laborious working up and purification processes.

WO 96/36597 describes the catalytic hydrogenation of nitro compounds using noble metal catalysts with the addition of a vanadium compound, while disclosing as end products free amines, but no lactams.

The aim of the present invention is to provide an improved process for preparing compounds of formula (I), particularly 7,8-dihydro-5H-pteridin-6-one derivatives.

DETAILED DESCRIPTION OF THE INVENTION

The present invention solves the problem outlined above by the method of synthesising compounds of formula (I) described hereinafter.

The invention thus relates to a process for preparing compounds of general formula I

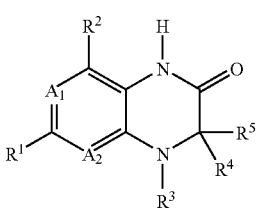

(I)

wherein $R^1$ denotes a group selected from the group consisting of chlorine, fluorine, bromine, methanesulphonyl, ethanesulphonyl, trifluoromethanesulphonyl, paratoluenesulphonyl, $CH_3S(\!=\!O)\!-\!$ and $phenylS(\!=\!O)\!-\!$ $R^2$ denotes hydrogen or $C_1$–$C_3$-alkyl, $R^3$ denotes hydrogen or a group selected from the group consisting of optionally substituted $C_1$–$C_{12}$-alkyl, $C_2$–$C_{12}$-alkenyl, $C_2$–$C_{12}$-alkynyl and $C_6$–$C_{14}$-aryl, or a group selected from the group consisting of optionally substituted and/or bridged $C_3$–$C_{12}$-Cycloalkyl, $C_3$–$C_{12}$-cycloalkenyl, $C_7$–$C_{12}$-polycycloalkyl, $C_7$–$C_{12}$-polycycloalkenyl, $C_5$–$C_{12}$-spirocycloalkyl and saturated or unsaturated $C_3$–$C_{12}$-heterocycloalkyl, which contains 1 to 2 heteroatoms, $R^4$, $R^5$ which may be identical or different denote hydrogen or optionally substituted $C_1$–$C_6$-alkyl, or $R^4$ and $R^5$ together denote a 2- to 5-membered alkyl bridge which may contain 1 to 2 heteroatoms, or $R^4$ and $R^3$ or $R^5$ and $R^3$ together denote a saturated or unsaturated $C_3$–$C_4$-alkyl bridge, which may optionally contain 1 heteroatom, and $A_1$ and $A_2$ which may be identical or different represent —CH= or —N=, preferably —N=, in which a compound of formula II

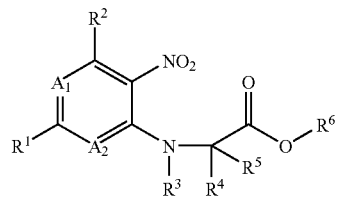

(II)

wherein $R^1$–$R^5$ and $A_1$, $A_2$ have the stated meaning and $R^6$ denotes $C_1$–$C_4$-alkyl, a) is hydrogenated with hydrogen in the presence of a hydrogenation catalyst and b) a copper, iron or vanadium compound is added, in which steps a) and b) may take place simultaneously or successively.

In a preferred process, the hydrogenation of the compound of formula II is carried out directly in the presence of the hydrogenation catalyst and the copper, iron or vanadium compound to form the compound of formula I.

In a particularly preferred process, after the first hydrogenation step a), first of all the intermediate product of formula III is obtained, which may optionally be isolated,

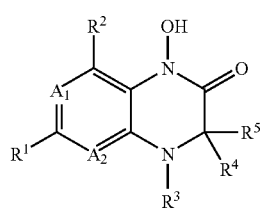

(III)

and is then further reduced in the presence of a hydrogenation catalyst and a copper, iron or vanadium compound to form a compound of formula I

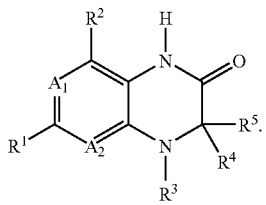

(I)

Also preferred is a process in which the hydrogenation catalyst is selected from the group consisting of rhodium, ruthenium, iridium, platinum, palladium and nickel, preferably platinum, palladium and Raney nickel. Platinum is particularly preferred. Platinum may be used in metallic form or oxidised form as platinum oxide on carriers such as e.g. activated charcoal, silicon dioxide, aluminium oxide, calcium carbonate, calcium phosphate, calcium sulphate, barium sulphate, titanium dioxide, magnesium oxide, iron oxide, lead oxide, lead sulphate or lead carbonate and optionally additionally doped with sulphur or lead. The preferred carrier material is activated charcoal, silicon dioxide or aluminium oxide.

Preferred copper compounds are compounds in which copper assumes oxidation states I or II, for example the halides of copper such as e.g. CuCl, $CuCl_2$, CuBr, $CuBr_2$, CuI or $CuSO_4$. Preferred iron compounds are compounds wherein iron assumes oxidation states II or III, for example the halides of iron such as e.g. $FeCl_2$, $FeCl_3$, $FeBr_2$, $FeBr_3$, $FeF_2$ or other iron compounds such as e.g. $FeSO_4$, $FePO_4$ or $Fe(acac)_2$.

Preferred vanadium compounds are compounds wherein vanadium assumes the oxidation states 0, II, III, IV or V, for example inorganic or organic compounds or complexes such as e.g. $V_2O_3$, $V_2O_5$, $V_2O_4$, $Na_4VO_4$, $NaVO_3$, $NH_4VO_3$, $VOCl_2$, $VOCl_3$, $VOSO_4$, $VCl_2$, $VCl_3$, vanadium oxobis(1-phenyl-1,3-butanedionate), vanadium oxotriisopropoxide, vanadium(III)acetylacetonate $[V(acac)_3]$ or vanadium(IV) oxyacetylacetonate $[VO(acac)_2]$. Vanadium(IV)oxyacetylacetonate $[VO(acac)_2]$ is particularly preferred The copper, iron or vanadium compound may be used either directly at the start of the hydrogenation or after the formation of the intermediate of formula (III), as preferred.

Also preferred is a process wherein the amount of added hydrogenation catalyst is between 0.1 and 10 wt.-% based on the compound of formula (II) used.

Also preferred is a process wherein the amount of copper, iron or vanadium compound used is between 0.01 and 10 wt.-% based on the compound of formula (II) used.

Also preferred is a process wherein the reaction is carried out in a solvent selected from the group consisting of dipolar, aprotic solvents, for example dimethylformamide, dimethylacetamide, N-methylpyrrolidinone, dimethylsulphoxide or sulpholane; alcohols, for example methanol, ethanol, 1-propanol, 2-propanol, the various isomeric alcohols of butane and pentane; ethers, for example diethyl ether, methyl-tert.-butylether, tetrahydrofuran, 2-methyltetrahydrofuran, dioxane or dimethoxyethane; esters, for example ethyl acetate, 2-propylacetate or 1-butylacetate; ketones, for example acetone, methylethylketone or methylisobutylketone; carboxylic acids, for example acetic acid; apolar solvents, for example toluene, xylene, cyclohexane or methylcyclohexane, as well as acetonitrile, methylene chloride and water. The solvents may also be used as mixtures.

Also preferred is a process wherein the reaction temperature is between 0° C. and 150° C., preferably between 20° C. and 100° C.

Also preferred is a process wherein the hydrogen pressure is 1 bar to 100 bar.

The invention further relates to a compound of formula (III)

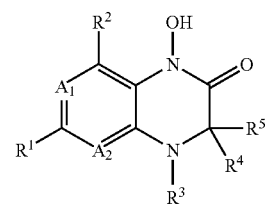

(III)

wherein $R^1$ to $R^5$ may have the stated meaning.

Preferred compounds of formula (III) are those wherein $A_1$ and $A_2$ are identical and denote —N=.

The reactions are worked up by conventional methods e.g. by extractive purification steps or precipitation and crystallisation methods.

The compounds according to the invention may be present in the form of the individual optical isomers, mixtures of the individual enantiomers, diastereomers or racemates, in the form of the tautomers as well as in the form of the free bases or the corresponding acid addition salts with acids—such as for example acid addition salts with hydrohalic acids, for example hydrochloric or hydrobromic acid, or organic acids, such as for example oxalic, fumaric, diglycolic or methanesulphonic acid.

Examples of alkyl groups, including those which are part of other groups, are branched and unbranched alkyl groups with 1 to 12 carbon atoms, preferably 1–6, particularly preferably 1–4 carbon atoms, such as for example: methyl, ethyl, propyl, butyl, pentyl, hexyl, heptyl, octyl, nonyl, decyl and dodecyl. Unless otherwise stated, the above-mentioned designations propyl, butyl, pentyl, hexyl, heptyl, octyl, nonyl, decyl and dodecyl include all the possible isomeric forms. For example the term propyl includes the two isomeric groups n-propyl and iso-propyl, the term butyl includes n-butyl, isobutyl, sec. butyl and tert.-butyl, the term pentyl includes isopentyl, neopentyl etc.

In the above-mentioned alkyl groups one or more hydrogen atoms may optionally be replaced by other groups. For example these alkyl groups may be substituted by fluorine. It is also possible for all the hydrogen atoms of the alkyl group to be replaced.

Examples of alkyl bridges, unless otherwise stated, are branched and unbranched alkyl groups with 2 to 5 carbon atoms, for example ethylene, propylene, isopropylene, n-butylene, iso-butyl, sec. butyl and tert.-butyl etc. bridges. Particularly preferred are ethylene, propylene and butylene bridges. In the above-mentioned alkyl bridges 1 to 2 C atoms may optionally be replaced by one or more heteroatoms selected from among oxygen, nitrogen or sulp Examples of alkenyl groups (including those which are part of other groups) are branched and unbranched alkylene groups with 2 to 12 carbon atoms, preferably 2–6 carbon atoms, particularly preferably 2–3 carbon atoms, provided that they have at least one double bond. The following are mentioned by way of example: ethenyl, propenyl, butenyl, pentenyl etc. Unless otherwise stated, the above-mentioned designations propenyl, butenyl etc. include all the possible isomeric forms. For example the term butenyl includes 1-butenyl, 2-butenyl, 3-butenyl, 1-methyl-1-propenyl, 1-methyl-2-propenyl, 2-methyl-1-propenyl, 2-methyl-2-propenyl and 1-ethyl-1-ethenyl.

In the above-mentioned alkenyl groups, unless otherwise described, one or more hydrogen atoms may optionally be replaced by other groups. For example these alkyl groups may be substituted by the halogen atom fluorine. It is also possible for all the hydrogen atoms of the alkenyl group to be replaced.

Examples of alkynyl groups (including those which are part of other groups) are branched and unbranched alkynyl groups with 2 to 12 carbon atoms, provided that they have at least one triple bond, for example ethynyl, propargyl, butynyl, pentynyl, hexynyl etc., preferably ethynyl or propynyl.

In the above-mentioned alkynyl groups, unless otherwise described, one or more hydrogen atoms may optionally be replaced by other groups. For example these alkyl groups may be fluorosubstituted. It is also possible for all the hydrogen atoms of the alkynyl group to be replaced.

The term aryl denotes an aromatic ring system with 6 to 14 carbon atoms, preferably 6 or 10 carbon atoms, preferably phenyl, which, unless otherwise described, may for example carry one or more of the following substituents: OH, $NO_2$, CN, OMe, —$OCHF_2$, —$OCF_3$, halogen, preferably fluorine or chlorine, $C_1$–$C_{10}$-alkyl, preferably $C_1$–$C_5$-alkyl, preferably $C_1$–$C_3$-alkyl, particularly preferably methyl or ethyl, —O—$C_1$–$C_3$-alkyl, preferably —O-methyl or —O-ethyl, —COOH, —COO—$C_1$–$C_4$-alkyl, preferably —O-methyl or —O-ethyl, —$CONH_2$.

Examples of cycloalkyl groups are cycloalkyl groups with 3-12 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally also carry one or more substituents, for example: OH, $NO_2$, CN, OMe, —$OCHF_2$, —$OCF_3$ or halogen, preferably fluorine or chlorine, $C_1$–$C_{10}$-alkyl, preferably $C_1$–$C_5$-alkyl, preferably $C_1$–$C_3$-alkyl, particularly preferably methyl or ethyl, —O—$C_1$–$C_3$-alkyl, preferably —O-methyl or —O-ethyl, —COOH, —COO—$C_1$–$C_4$-alkyl, preferably —COO-methyl or —COO-ethyl or —$CONH_2$. Particularly preferred substituents of the cycloalkyl groups are =O, OH, methyl or F.

Examples of cycloalkenyl groups are cycloalkyl groups with 3-12 carbon atoms, which have at least one double bond, for example cyclopropenyl, cyclobutenyl, cyclopentenyl, cyclohexenyl or cycloheptenyl, preferably cyclopropenyl, cyclopentenyl or cyclohexenyl, while each of the above-mentioned cycloalkenyl groups may optionally also carry one or more substituents.

"=O" denotes an oxygen atom linked by a double bond.

Examples of heterocycloalkyl groups are, unless otherwise described in the definitions, 3- to 12-membered, preferably 5-, 6- or 7-membered, saturated or unsaturated heterocycles, which may contain nitrogen, oxygen or sulphur as heteroatoms, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole and pyrazolidine, preferably morpholine, pyrrolidine, piperidine or piperazine, while the heterocycle may optionally carry substituents, for example $C_1$–$C_4$-alkyl, preferably methyl, ethyl or propyl.

Examples of polycycloalkyl groups are optionally substituted, bi-, tri-, tetra- or pentacyclic cycloalkyl groups, for example pinane, 2,2,2-octane, 2,2,1-heptane or adamantane. Examples of polycycloalkenyl groups are optionally bridged and/or substituted, 8- membered bi-, tri-, tetra- or pentacyclic cycloalkenyl groups, preferably bicycloalkenyl or tricycloalkenyl groups, if they contain at least one double bond, for example norbornene.

Examples of spiroalkyl groups are optionally substituted spirocyclic $C_5$–$C_{12}$ alkyl groups.

Halogen generally denotes fluorine, chlorine, bromine or iodine, preferably fluorine, chlorine or bromine, particularly preferably chlorine.

The substituent $R^1$ may represent a group selected from the group consisting of chlorine, fluorine, bromine, methanesulphonyl, ethanesulphonyl, trifluoromethanesulphonyl and para-toluenesulphonyl, preferably chlorine.

The substituent $R^2$ may represent hydrogen or $C_1$–$C_3$-alkyl, preferably hydrogen.

The substituent $R^3$ may represent hydrogen,
or a group selected from the group consisting of optionally substituted $C_1$–$C_{12}$-alkyl, $C_2$–$C_{12}$-alkenyl, $C_2$–$C_{12}$-alkynyl, and $C_6$–$C_{14}$-aryl, preferably phenyl,
or a group selected from the group consisting of optionally substituted and/or bridged $C_3$–$C_{12}$-Cycloalkyl, preferably cyclopentyl, $C_3$–$C_{12}$-cycloalkenyl, $C_7$–$C_{12}$-polycycloalkyl, $C_7$–$C_{12}$-polycycloalkenyl, $C_5$–$C_{12}$-spirocycloalkyl and saturated or unsaturated $C_3$–$C_{12}$-heterocycloalkyl, which contains 1 to 2 heteroatoms.

The substituents $R^4$, $R^5$ may be identical or different and may represent hydrogen,
or optionally substituted $C_1$–$C_6$-alkyl,
or $R^4$ and $R^5$ together represent a 2- to 5-membered alkyl bridge which may contain 1 to 2 heteroatoms,
or $R^4$ and $R^3$ or $R^5$ and $R^3$ together represent a saturated or unsaturated $C_3$–$C_4$-alkyl bridge, which may optionally contain 1 heteroatom.

$A_1$ and $A_2$ which may be identical or different represent —CH= or —N=, preferably —N=.

$R^6$ may represent a $C_1$–$C_4$-alkyl, preferably methyl or ethyl.

The compound of formula (II) may be prepared according to methods known from the literature, for example analogously to the syntheses described in WO 03/020722.

The compounds of general formula (I) may be prepared inter alia analogously to the following examples of synthesis. These Examples are, however, intended only as examples of procedures to illustrate the invention, without restricting it to their content. The general synthesis is shown in Scheme (1).

Scheme 1

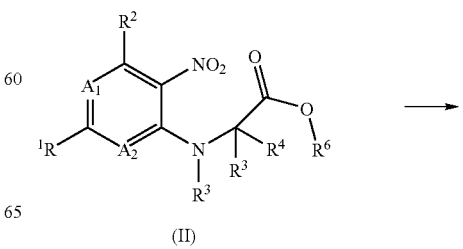

(II)

-continued

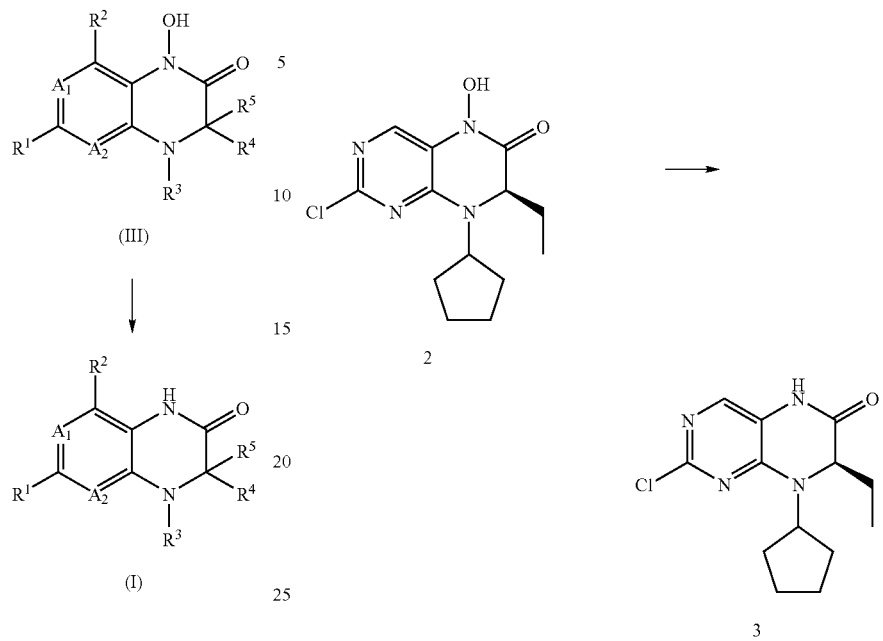

Synthesis of (7R)-2-chloro-8-cyclopentyl-7-ethyl-5-hydroxy-7,8-dihydro-5H-pteridin-6-one

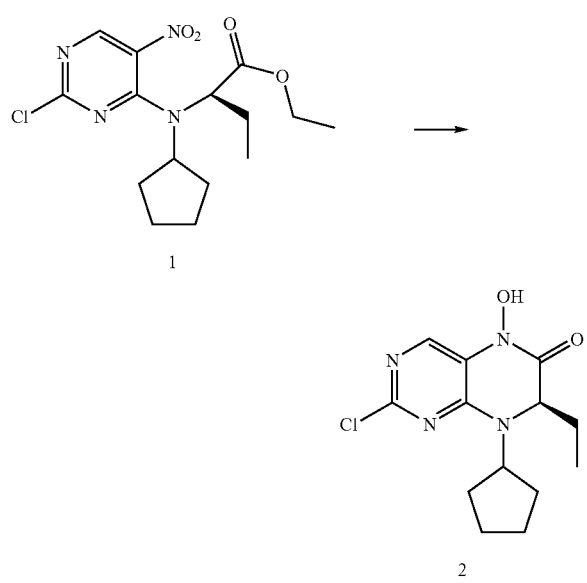

30 g (84.2 mmol) of 1 are dissolved in 300 ml of tetrahydrofuran and 3 g Pt/C (5%) are added. The reaction mixture is hydrogenated for 5 h at 35° C. and a hydrogen pressure of 4 bar. The catalyst is filtered off and washed with approx. 30 ml of tetrahydrofuran. The filtrate is concentrated by evaporation under reduced pressure. 25.6 g of product 2 are obtained as a yellow solid.

$^1$H-NMR (400 MHZ) (DMSO$_{d6}$): δ 11.05 (bs 1H); 7.85 (s 1H); 4.47–4.45 (dd 1H); 4.16–4.08 (t 1H); 1.95–1.67 (m 10H); 0.80–0.73 (t 3H)

Synthesis of (7R)-2-chloro-8-cyclopentyl-7-ethyl-7,8-dihydro-5H-pteridin-6-one 5.22 g (17.6 mmol) of 2 are dissolved in 55 ml of tetrahydrofuran. 520 mg Pt-C (5%) and 250 mg vanadium (IV)oxyacetylacetonate are added. The reaction mixture is hydrogenated for 6 hours at 20° C. and a hydrogen pressure of 4 bar. The catalyst is filtered off and washed with approx. 15 ml of tetrahydrofuran. The filtrate is concentrated by evaporation under reduced pressure.

5.0 g of product 3 are obtained as a yellow powder.

$^1$H-NMR (400 MHz) (DMSO$_{d6}$): δ 11.82 (bs 1H); 7.57 (s 1H); 4.24–4.21 (dd 1H); 4.17–4.08 (m 1H); 1.97–1.48 (m 10H); 0.80–0.77 (t 3H).

Synthesis of: (7R)-2-chloro-8-cyclopentyl-7-ethyl-7,8-dihydro-5H-pteridin-6-one 70 g Pt/C (5%) are added to a solution of 700 g (1.96 mol) of 1 in 700 ml of tetrahydrofuran. The reaction mixture is hydrogenated for 2.5 hours at 35° C. and a hydrogen pressure of 4 bar until the hydrogen uptake has stopped. The autoclave is opened and 35 g vanadium(IV)oxyacetylacetonate are added. The mixture is hydrogenated for a further 2.5 hours at 35° C. and a hydrogen pressure of 4 bar. It is filtered and the residue is washed with tetrahydrofuran. The filtrate is concentrated by evaporation under reduced pressure. The residue is dissolved in 2.75 L acetone and precipitated by the addition of an equal amount of demineralised water. The solid is suction filtered and washed with an acetone/water mixture (1:1), then with tert.-butylmethylether. After drying 551 g of product 3 are obtained.

Synthesis of: (7R)-2-chloro-8-cyclopentyl-7-ethyl-7,8-dihydro-5H-pteridin-6-one 30 g (84 mmol) of 1 are dissolved in 300 ml of tetrahydrofuran. 3 g Pt/C (5%) and 1.5 g vanadium(IV)oxyacetylacetonate are added. The reaction mixture is hydrogenated for 24 hours at 35° C. and a hydrogen pressure of 4 bar until the reaction is complete. It is filtered, the residue is washed with tetrahydrofuran and the filtrate is concentrated by evaporation under reduced pressure. The residue is dissolved in 118 ml acetone and precipitated by the addition of an equal amount of demineralised water. The solid is suction filtered and washed with an acetone/water mixture (1:1) and then with tert.-butylmethylether. After drying 18 g of product 3 are obtained.

Synthesis of: (7R)-2-chloro-7-ethyl-8-isopropyl-7,8-dihydro-5H-pteridin-6-one

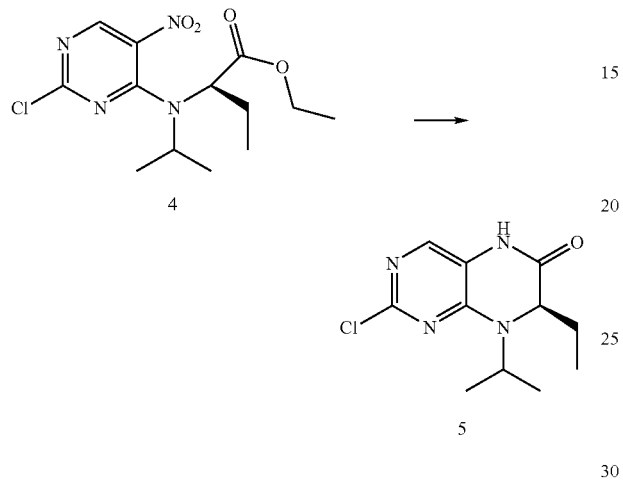

10 g (316 mmol) of 4 are dissolved in 800 ml of tetrahydrofuran and 200 ml isopropanol. 10 g Pt/C (5%) and 5 g vanadium(IV)oxyacetylacetonate are added. The reaction mixture is hydrogenated for 24 hours at 35° C. and a hydrogen pressure of 4 bar until the reaction is complete. It is filtered and the filtrate is evaporated down until crystallisation sets in. 150 ml isopropanol are added and the suspension is heated to 70–80° C. until fully dissolved. After the addition of 600 ml demineralised water the product is brought to crystallisation. It is suction filtered and washed with demineralised water. After drying 68 g of product 5 are obtained.

$^{1}$H-NMR (400 MHz) (DMSO$_{d6}$): δ 10.81 (bs 1H); 7.56 (s 1H); 4.37–4.24 (m 2H); 1.89–1.65 (m 2H); 1.34–1.31 (m 6H); 0.80–0.73 (t 3H)

What is claimed is:

1. A Process for preparing compounds of the formula I

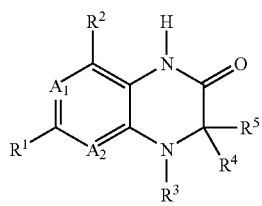

wherein

R$^{1}$ denotes a group selected from the group consisting of chlorine, fluorine, bromine, methanesulphonyl, ethanesulphonyl, trifluoromethanesulphonyl, para-toluenesulphonyl, CH$_{3}$S(=O)— and phenylS(=O)—, R$^{2}$ denotes hydrogen or C$_{1}$–C$_{3}$-alkyl, R$^{3}$ denotes hydrogen or a group selected from the group consisting of optionally substituted C$_{1}$–C$_{12}$-alkyl, C$_{2}$–C$_{12}$-alkenyl, C$_{2}$–C$_{12}$-alkynyl and C$_{6}$–C$_{14}$-aryl, or a group selected from the group consisting of optionally substituted and/or bridged C$_{3}$–C$_{12}$-cycloalkyl, C$_{3}$–C$_{12}$-cycloalkenyl, C$_{7}$–C$_{12}$-polycycloalkyl, C$_{7}$–C$_{12}$-polycycloalkenyl, C$_{5}$–C$_{12}$-spirocycloalkyl and saturated or unsaturated C$_{3}$–C$_{12}$-heterocycloalkyl, which contains 1 to 2 heteroatoms, R$^{4}$, R$^{5}$ which may be identical or different denote hydrogen or optionally substituted C$_{1}$–C$_{6}$-alkyl, or R$^{4}$ and R$^{5}$ together denote a 2- to 5-membered alkyl bridge, which may contain 1 to 2 heteroatoms, or R$^{4}$ and R$^{3}$ or R$^{5}$ and R$^{3}$ together denote a saturated or unsaturated C$_{3}$–C$_{4}$-alkyl bridge, which may optionally contain 1 heteroatom, and "A1 and A2 denote —N=", comprising a) hydrogenating with hydrogen in the presence of a hydrogenation catalyst and a compound of formula II

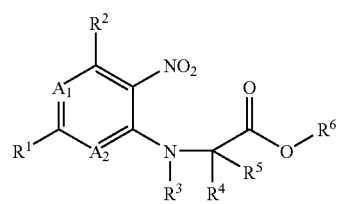

wherein

R$^{1}$ to R$^{5}$, A$_{1}$ and A$_{2}$ have the meanings given above and R$^{6}$ denotes C$_{1}$–C$_{4}$-alkyl, and b) adding a copper, iron or vanadium compound, wherein in which steps a) and b) may take place simultaneously or successively step b) followed by step a).

2. The Process according to claim 1, wherein in step b) a copper compound is added.

3. The Process according to claim 1, wherein in step b) an iron compound is added.

4. The Process according to claim 1, wherein in step b) a vanadium compound is added.

5. The Process according to claim 1 wherein steps a) and b) are carried out successively.

6. The Process according to claim 5, wherein that after the first step a) the intermediate product of formula III is first obtained, which may optionally be isolated,

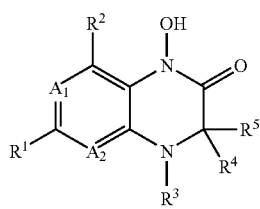

and after the subsequent step b) a compound of formula I is obtained.

7. The Process according to claim 1, wherein steps a) and b) are carried out simultaneously.

8. The Process according to claim 1, wherein the hydrogenation catalyst is selected from the group consisting of rhodium, ruthenium, iridium, platinum, palladium and nickel.

9. The Process according to claim 1, wherein the amount of hydrogenation catalyst added is between 0.1 and 10 wt.-%, based on the compound of formula (II) used.

10. The Process according to claim 1, wherein the amount of copper, iron or vanadium compound added is between 0.01 and 10 wt-%, based on the compound of formula (II) used.

11. The Process according to claim 1, wherein the reaction is carried out in a solvent or mixture of solvents selected from the group consisting of dipolar, aprotic solvents, alcohols, ethers, esters, carboxylic acids, apolar solvents, acetonitrile, methylene chloride and water.

12. The Process according to claim 1, wherein the reaction temperature is between 0° C. and 150° C.

13. The Process according to claim 1, wherein the hydrogen pressure is from 1 bar to 100 bar.

14. A Process for preparing compounds of the formula I

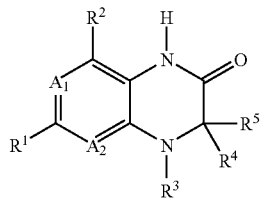
(I)

wherein
$R^1$ denotes a group selected from the group consisting of chlorine, fluorine, bromine, methanesulphonyl, ethanesulphonyl, trifluoromethanesulphonyl, para-toluenesulphonyl, $CH_3S(=O)-$ and $phenylS(=O)-$,
$R^2$ denotes hydrogen or $C_1-C_3$-alkyl,
$R^3$ denotes hydrogen or a group selected from the group consisting of optionally substituted C1–C12-alkyl, C2–C12-alkenyl, C2–C12-alkynyl and $C_6-C_{14}$-aryl, or a group selected from the group consisting of optionally substituted and/or bridged $C_3-C_{12}$-cycloalkyl, $C_3-C_{12}$-cycloalkenyl, $C_7-C_{12}$-polycycloalkyl, $C_7-C_{12}$-polycycloalkenyl, $C_5-C_{12}$-spirocycloalkyl and saturated or unsaturated $C_3-C_{12}$-heterocycloalkyl, which contains 1 to 2 heteroatoms,
$R^4$, $R^5$ which may be identical or different denote hydrogen or optionally substituted $C_1-C_6$-alkyl, or
$R^4$ $R^5$ together denote a 2- to 5-membered alkyl bridge, which may contain 1 to 2 heteroatoms, or
$R^4$ and $R^3$ or $R^5$ and $R^3$ together denote a saturated or unsaturated $C_3-C_4$-alkyl bridge, which may optionally contain 1 heteroatom, and
$A_1$ and $A_2$ denote $-N=$, comprising
hydrogenating a compound of formula III with hydrogen in the presence of a hydrogenation catalyst and a copper, iron or vanadium compound

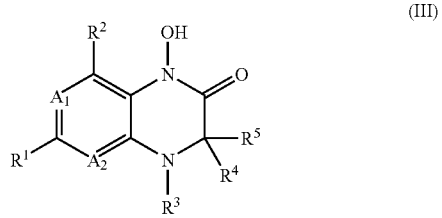
(III)

wherein
$R^1$ to $R^5$ and $A_1$, $A_2$ have the meanings given above in this claim.

* * * * *